United States Patent
Kim

(10) Patent No.: US 8,961,419 B2
(45) Date of Patent: Feb. 24, 2015

(54) ULTRASOUND DIAGNOSTIC SYSTEM WITH SELECTIVE DISPLAY OF IMAGES BASED ON VIEWING ANGLE

(75) Inventor: Dae Young Kim, Chuncheon-si (KR)

(73) Assignee: Samsung Medison Co., Ltd., Hongcheon-Gun, Gangwon-Do (KR)

( * ) Notice: Subject to any disclaimer, the term of this patent is extended or adjusted under 35 U.S.C. 154(b) by 187 days.

(21) Appl. No.: 12/959,215

(22) Filed: Dec. 2, 2010

(65) Prior Publication Data

US 2011/0144488 A1    Jun. 16, 2011

(30) Foreign Application Priority Data

Dec. 11, 2009    (KR) ........................ 10-2009-0122852

(51) Int. Cl.
| | | |
|---|---|---|
| *A61B 8/00* | (2006.01) | |
| *G02B 27/22* | (2006.01) | |
| *G01S 7/52* | (2006.01) | |
| *G02B 27/02* | (2006.01) | |
| *G02B 27/01* | (2006.01) | |

(52) U.S. Cl.
CPC ............ *A61B 8/463* (2013.01); *G02B 27/2214* (2013.01); *G01S 7/52053* (2013.01); *G02B 27/022* (2013.01); *G02B 2027/0129* (2013.01)
USPC ................................ 600/440; 348/51; 349/15

(58) Field of Classification Search
USPC ...................... 600/437, 443, 459; 348/51, 54; 715/700; 345/32
See application file for complete search history.

(56) References Cited

U.S. PATENT DOCUMENTS

| | | | | |
|---|---|---|---|---|
| 5,993,391 A | * | 11/1999 | Kamiyama | 600/443 |
| 6,753,858 B2 | * | 6/2004 | Asai et al. | 345/419 |
| 6,801,263 B2 | * | 10/2004 | Sato et al. | 349/15 |
| 7,563,228 B2 | * | 7/2009 | Ma et al. | 600/437 |
| 7,697,203 B2 | * | 4/2010 | Cha et al. | 359/465 |
| 8,174,464 B2 | * | 5/2012 | Choi et al. | 345/6 |
| 2003/0001993 A1 | * | 1/2003 | Iijima | 349/113 |
| 2005/0174528 A1 | * | 8/2005 | Kubo et al. | 349/193 |
| 2005/0206814 A1 | * | 9/2005 | Histake | 349/112 |
| 2005/0264560 A1 | * | 12/2005 | Hartkop et al. | 345/419 |
| 2006/0173338 A1 | * | 8/2006 | Ma et al. | 600/456 |
| 2007/0073149 A1 | * | 3/2007 | Kelly et al. | 600/437 |
| 2012/0032997 A1 | * | 2/2012 | Cha et al. | 345/690 |

FOREIGN PATENT DOCUMENTS

KR    10-2007-0110965 A    11/2007
KR    10-2008-005305 A    6/2008

OTHER PUBLICATIONS

Korean Office Action issued in Korean Patent Application No. KR 10-2009-0122852 dated Mar. 25, 2011.

* cited by examiner

*Primary Examiner* — Unsu Jung
*Assistant Examiner* — Amanda Lauritzen Moher
(74) *Attorney, Agent, or Firm* — McDermott Will & Emery LLP

(57) ABSTRACT

An ultrasound diagnostic system is disclosed. The ultrasound diagnostic system allows an examiner and an examinee to view a diagnosis result on different screens through a single display unit by adjusting viewing angles depending on positions of the examiner and the examinee, thereby providing a screen for the current diagnosis status to the examinee without a separate monitor for the examinee and providing an optimized screen for diagnosis to the examiner.

3 Claims, 5 Drawing Sheets

ULTRASOUND DIAGNOSTIC SYSTEM WITH SELECTIVE DISPLAY OF IMAGES BASED ON VIEWING ANGLE

CROSS REFERENCE TO RELATED APPLICATIONS

This application claims the benefit of Korean Patent Application No. 10-2009-0122852, filed Dec. 11, 2009, the entire contents of which are incorporated herein by reference.

BACKGROUND OF THE INVENTION

1. Field of the Invention

The present invention relates to an ultrasound diagnostic system and, more particularly, to an ultrasound diagnostic system that allows an examiner and an examinee to view a diagnosis result on different screens through a single display unit by adjusting viewing angles depending on positions of the examiner and the examinee.

2. Description of the Related Art

Generally, an ultrasound diagnostic system refers to a non-invasive apparatus that irradiates an ultrasound signal from a surface of a patient body towards a target internal organ beneath the body surface and obtains an image of a monolayer or blood flow in soft tissue from information in the reflected ultrasound signal (ultrasound echo-signal). The ultrasound diagnostic system has been widely used for diagnosis of the heart, the abdomen, the urinary organs, and in obstetrics and gynecology due to various merits such as small size, low price, real-time image display, and high stability through elimination of radiation exposure, as compared with other image diagnostic systems, such as X-ray diagnostic systems, computerized tomography scanners (CT scanners), magnetic resonance imagers (MRIs), nuclear medicine diagnostic apparatuses, and the like.

The ultrasound diagnostic system transmits an ultrasound signal to a diagnosis target, receives the ultrasound echo-signal reflected therefrom, and displays an ultrasound image, particularly, a two-dimensional grey-scale ultrasound image, on a monitor, which corresponds to a display mode, for example, B-mode, M-mode, Doppler mode, etc., based on the received echo-signal. It should be noted that the above description is provided for understanding the background of the invention and is not a description of a conventional technique.

In diagnosis with the ultrasound diagnostic system, two monitors are used to provide a diagnosis result to both an examiner and an examinee such that the monitors for the examiner and the examinee display the same image or such that the monitor for the examiner displays all necessary information for diagnosis and the monitor for to the examinee displays only an image of the diagnosis result.

As such, separate monitors are needed to provide the diagnosis result to both the examiner and the examinee.

SUMMARY OF THE INVENTION

The present invention is conceived to solve the problem of the related art as described above, and an aspect of the invention is to provide an ultrasound diagnostic system that allows an examiner and an examinee to view a diagnosis result on different screens through a single display unit by adjusting viewing angles depending on positions of the examiner and the examinee.

In accordance with one aspect of the invention, an ultrasound diagnostic system includes: an ultrasound diagnostic unit configured to transmit an ultrasound signal to an examinee and to receive the ultrasound signal reflected from the examinee to generate an ultrasound image of the examinee; a display unit comprising a plurality of barrier layers; a viewing angle selection unit configured to select viewing angles depending on positions of an examiner and the examinee; a switching unit configured to selectively activate the plurality of barrier layers in response to a selection of the selection unit; an image processor configured to mix and output a plurality of images to the display unit depending on the viewing angles selected by the viewing angle selection unit to independently provide diagnosis information and the ultrasound images generated by the ultrasound diagnostic unit to the examiner and the examinee; and a controller configured to control the ultrasound diagnostic unit and the image processor in response to a selection of the examiner.

The barrier layers may be barrier layers of a parallax barrier type.

The barrier layers may include at least a longitudinal stripe-shaped barrier layer, a transverse stripe-shaped barrier layer, and a diagonal stripe-shaped barrier layer.

BRIEF DESCRIPTION OF THE DRAWINGS

The above and other aspects, features and advantages of the invention will become apparent from the following description of embodiments given in conjunction with the accompanying drawings, in which.

DETAILED DESCRIPTION OF THE EMBODIMENT

Exemplary embodiments of the invention will now be described in detail with reference to the accompanying drawings. It should be noted that the drawings are not to precise scale and may be exaggerated in thickness of lines or size of components for descriptive convenience and clarity only. Furthermore, terms used herein are defined by taking functions of the invention into account and can be changed according to the custom or intention of users or operators. Therefore, definition of the terms should be made according to overall disclosures set forth herein.

Figure 1:
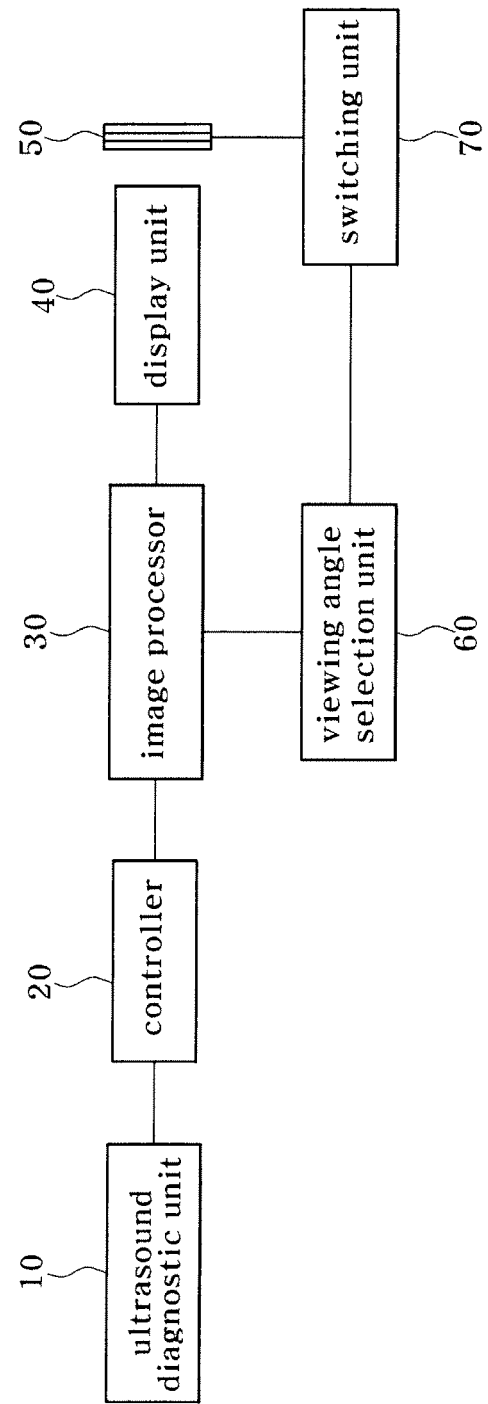
FIG. 1 is a block diagram of an ultrasound diagnostic system according to one embodiment of the present invention.
Figure 2:
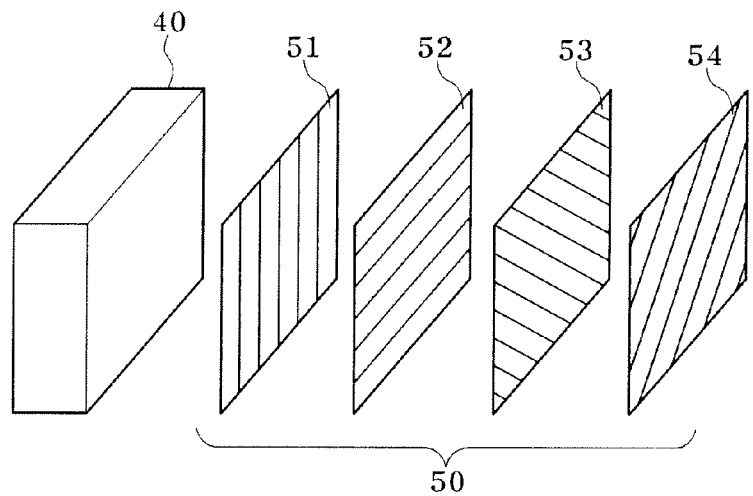
FIG. 2 illustrates barrier layers of the ultrasound diagnostic system according to the embodiment of the present invention.
Figure 3:
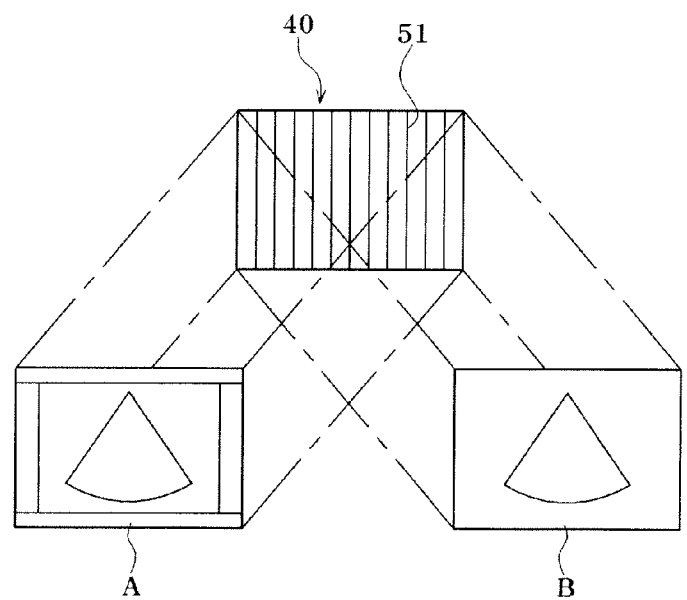
FIG. 3 illustrates two screens viewed at right and left sides in the ultrasound diagnostic system according to the embodiment of the present invention.
Figure 4:
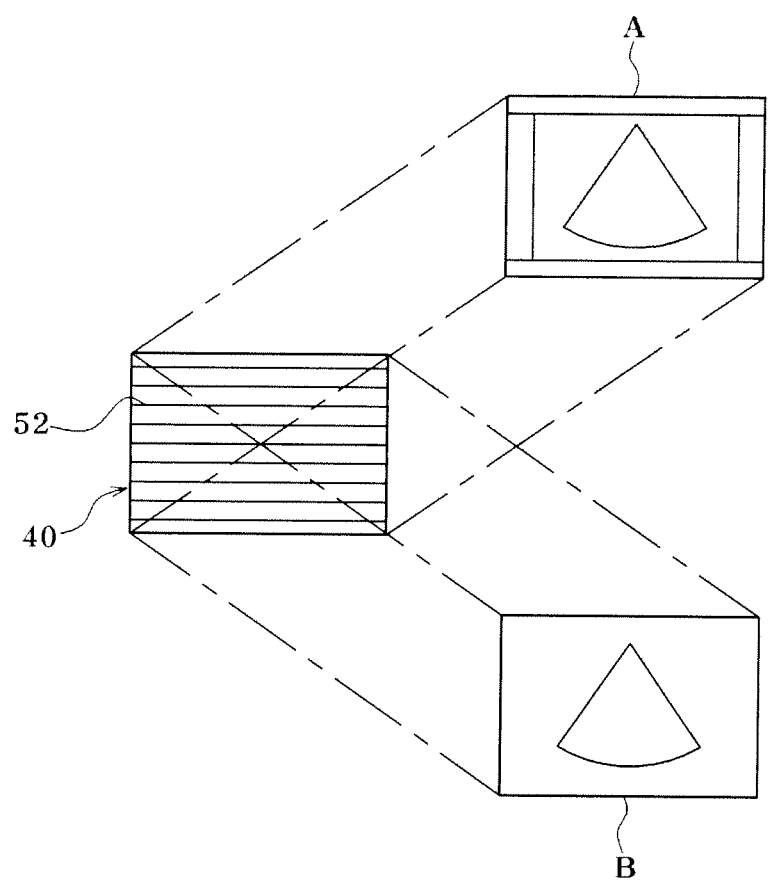
FIG. 4 illustrates two screens viewed at upper and lower sides in the ultrasound diagnostic system according to the embodiment of the present invention.
Figure 5:
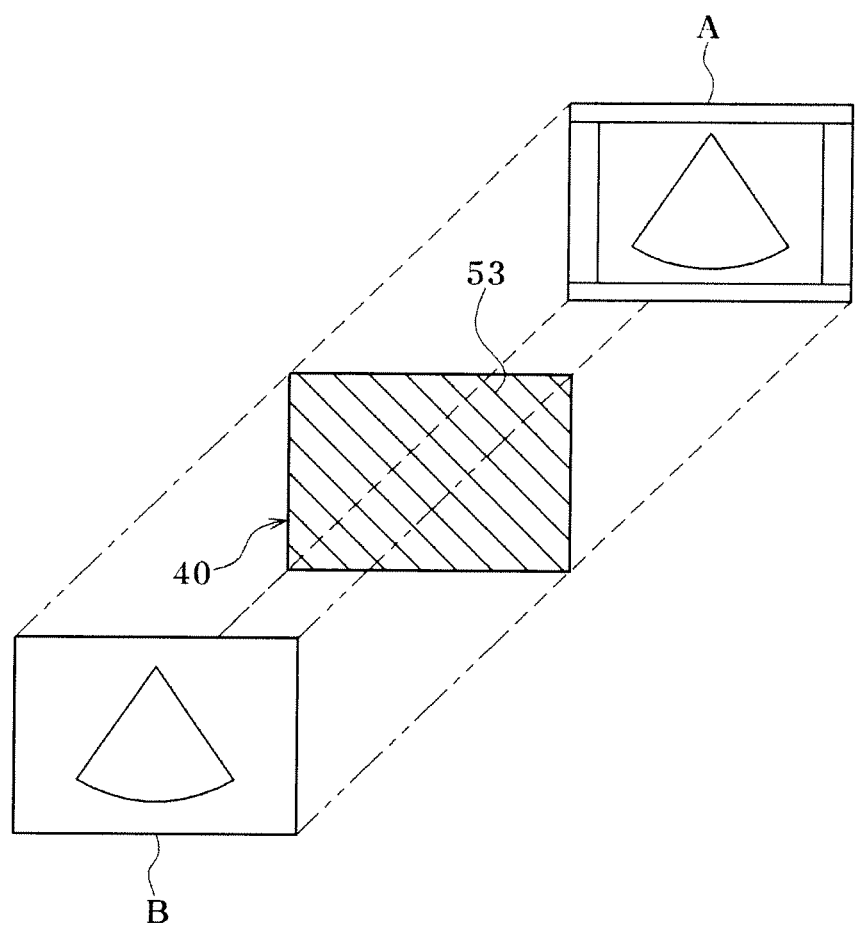
FIGS. 5 and 6 illustrate two screens diagonally viewed in the ultrasound diagnostic system according to the embodiment of the present invention.
Figure 6:
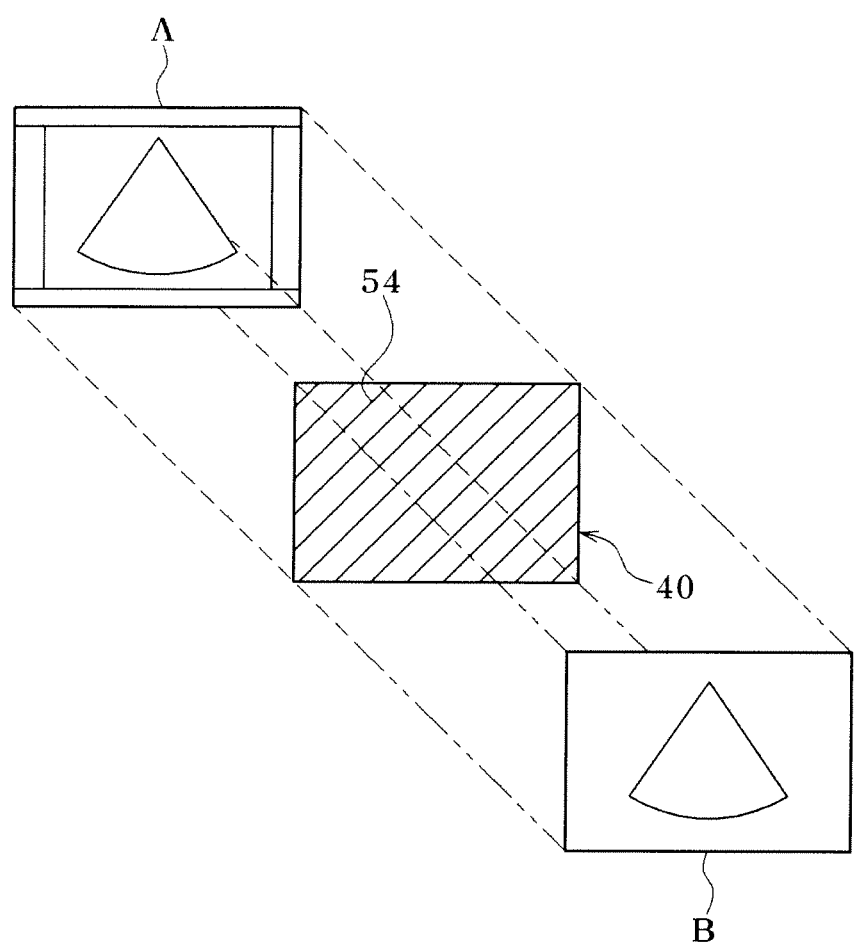

FIG. 1 is a block diagram of an ultrasound diagnostic system according to one embodiment, FIG. 2 illustrates barrier layers of the ultrasound diagnostic system according to the embodiment, FIG. 3 illustrates two screens viewed at right and left sides in the ultrasound diagnostic system according to the embodiment, FIG. 4 illustrates two screens viewed at upper and lower sides in the ultrasound diagnostic system according to the embodiment, and FIGS. 5 and 6 illustrate two screens diagonally viewed in the ultrasound diagnostic system according to the embodiment.

Referring to FIG. 1, an ultrasound diagnostic system 100 of this embodiment includes an ultrasound diagnostic unit 10, a display unit 40, a viewing angle selection unit 60, a switching unit 70, an image processor 30, and a controller 20.

The ultrasound diagnostic unit 10 transmits an ultrasound signal to an examinee and receives the ultrasound signal reflected from the examinee to generate an ultrasound image of the examinee.

As shown in FIG. 2, the display unit 40 includes a plurality of barrier layers of a parallax barrier type formed by overlapping a longitudinal stripe-shaped barrier layer 51, a transverse stripe-shaped barrier layer 52 and diagonal stripe-shaped barrier layers 53, 54 on top of one another.

The viewing angle selection unit 60 selects viewing angles depending on positions of an examiner and the examinee. In other words, the viewing angle selection unit 60 selects viewing angles at which the examiner and the examinee view the single display unit 40.

The switching unit 70 selectively activates the plurality of barrier layers in response to a selection of the selection unit 60. For example, when an examiner is located at a right or left side of an examinee lying on a table in the diagnostic system, the switching unit 70 activates the diagonal stripe-shaped barrier layer 54 as well as the longitudinal stripe-shaped barrier layer 51.

The image processor 30 mixes and outputs a plurality of images to the display unit 40 depending on the viewing angles selected by the viewing angle selection unit 60 to independently provide diagnosis information and the ultrasound images generated by the ultrasound diagnostic unit 10 to the examiner and the examinee.

The controller 20 controls the ultrasound diagnostic unit 10 and the image processor 30 in response to a selection of the examiner.

As such, when an examiner wishes to provide the diagnostic status to an examinee during diagnosis with the ultrasound diagnostic unit, viewing angles of the examiner and the examinee are selected through the viewing angle selection unit 60, and the image processor 30 mixes and outputs images for the examiner and the examinee to the display unit 40 such that the images are independently provided to the examiner and the examinee through the barrier layers 50.

In FIG. 3, when an examiner and an examinee are located at left and right sides in the diagnostic system, the longitudinal stripe-shaped barrier layer 51 is activated through the viewing angle selection unit 60 to allow the display unit 40 to display a screen, which is viewed from the left side by the examiner as Screen A providing information for both diagnosis and a diagnosis result and is viewed from the right side by the examinee as Screen B providing only the diagnosis result, so that the examiner and the examinee can see the independent screens through the single display unit 40.

In FIG. 4, when an examiner and an examinee are located at upper and lower sides in the diagnostic system, the transverse stripe-shaped barrier layer 52 is activated through the viewing angle selection unit 60 to allow the display unit 40 to display a screen, which is viewed from the upper side by the examiner as Screen A providing information for both diagnosis and a diagnosis result and is viewed from the lower side by the examinee as Screen B providing only the diagnosis result, so that the examiner and the examinee can see the independent screens through the single display unit 40.

Further, in FIGS. 5 and 6, when an examiner and an examinee are diagonally located in the diagnostic system, the diagonal stripe-shaped barrier layers 53, 54 are activated through the viewing angle selection unit 60 to allow the display unit 40 to display a screen, which is viewed from a lateral upper side by the examiner as Screen A providing information for both diagnosis and a diagnosis result and is viewed from a lateral lower side by the examinee as Screen B providing only the diagnosis result, so that the examiner and the examinee can see the independent monitors through the single display unit 40.

As such, the ultrasound diagnostic system of the embodiment can realize dual screens to be independently provided to both an examiner and an examinee through the single display unit 40 wherever the examiner and the examinee are positioned in the ultrasound diagnostic system.

According to the embodiment, the ultrasound diagnostic system allows an examiner and an examinee to view a diagnosis result on different screens through a single display unit by adjusting viewing angles depending on positions of the examiner and the examinee, thereby providing a screen for the current diagnosis status to the examinee without a separate monitor for the examinee and providing an optimized screen for diagnosis to the examiner.

Although some embodiments have been provided to illustrate the invention in conjunction with the drawings, it will be apparent to those skilled in the art that the embodiments are given by way of illustration only, and that various modifications and equivalent embodiments can be made without departing from the spirit and scope of the invention. The scope of the invention should be limited only by the accompanying claims.

What is claimed is:

1. An ultrasound diagnostic system comprising:
   an ultrasound diagnostic unit;
   a display comprising a plurality of barrier layers overlapping each other; and
   a switch configured to selectively activate at least one of the plurality of barrier layers in response to selected viewing angles,
   wherein at least a barrier layer among the plurality of barrier layers comprises a diagonal lattice-shaped barrier layer, with the diagonal being relative to a length and a width of the layer,
   wherein at least one of the remaining barrier layers among the plurality of barrier layers comprises a lattice-shape which is not diagonal,
   wherein the selected viewing angles depend on positions of a plurality of viewers relative to the display, and
   wherein the display displays different images to the plurality of viewers depending on the positions of the plurality of viewers.

2. The ultrasound diagnostic system according to claim 1, wherein the barrier layers are barrier layers of a parallax barrier type.

3. The ultrasound diagnostic system according to claim 1, wherein the barrier layers further comprise at least a longitudinal lattice-shaped barrier layer and a transverse lattice-shaped barrier layer.

* * * * *